(12) United States Patent
Cottrell

(10) Patent No.: US 6,271,428 B1
(45) Date of Patent: *Aug. 7, 2001

(54) PROCESS FOR THE PURIFICATION OF A DIOLEFIN HYDROCARBON STREAM

(75) Inventor: Paul R. Cottrell, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/358,795

(22) Filed: Jul. 22, 1999

(51) Int. Cl.⁷ ..................................... C07C 5/08
(52) U.S. Cl. ................ 585/259; 585/258; 585/810; 208/296
(58) Field of Search ................. 585/258, 259, 585/810; 208/296

(56) References Cited

U.S. PATENT DOCUMENTS

| | | | |
|---|---|---|---|
| 3,407,227 | * 10/1968 | Beck et al. | 554/144 |
| 3,496,069 | * 2/1970 | Tschopp et al. | 203/53 |
| 3,634,536 | 1/1972 | Frevel et al. | 260/681.5 R |
| 3,637,888 | * 1/1972 | Cahn et al. | 585/259 |
| 3,655,806 | * 4/1972 | Brandt et al. | 585/803 |
| 3,692,852 | * 9/1972 | Tabler | 585/274 |
| 3,751,508 | * 8/1973 | Fugiso et al. | 585/262 |
| 3,912,789 | * 10/1975 | Frevel et al. | 585/259 |
| 4,049,742 | * 9/1977 | Weitz et al. | 585/285 |
| 4,277,313 | * 7/1981 | Mehra et al. | 203/32 |
| 4,440,956 | 4/1984 | Couvillion | 585/260 |
| 4,831,200 | * 5/1989 | Debras et al. | 585/259 |
| 6,040,489 | * 3/2000 | Imai | 55/260 |

* cited by examiner

Primary Examiner—Walter D. Griffin
Assistant Examiner—Nadine Preisch
(74) Attorney, Agent, or Firm—John G. Tolomei; John G. Cutts, Jr.

(57) ABSTRACT

A process for the selective hydrogenation of trace quantities of acetylene compounds contained in a stream of diolefins to achieve extended on-stream performance by simultaneously contacting the selective catalyst with a diolefin feed, hydrogen and a polymer solvent.

5 Claims, 1 Drawing Sheet

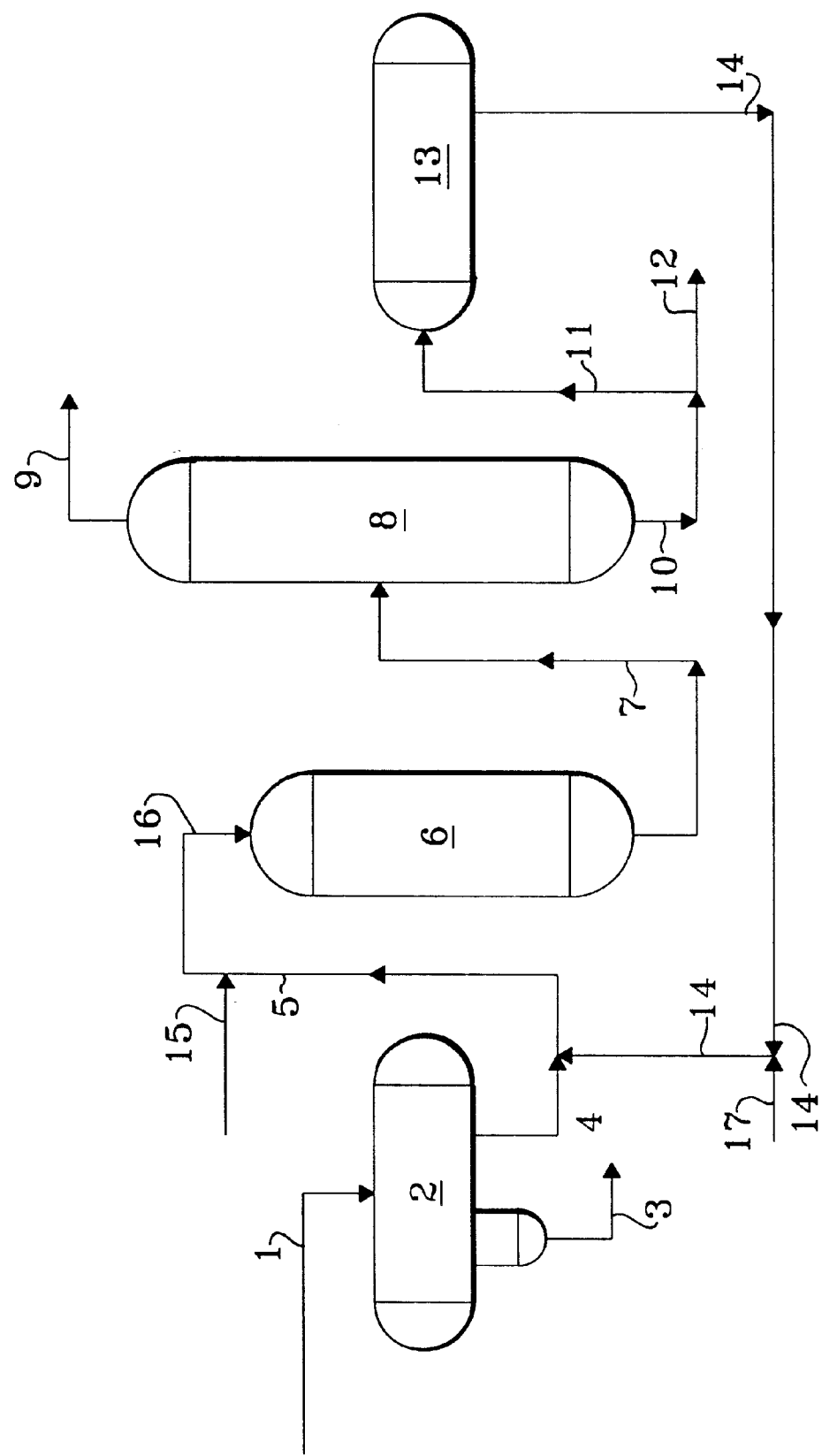

PROCESS FOR THE PURIFICATION OF A DIOLEFIN HYDROCARBON STREAM

BACKGROUND OF THE INVENTION

The field of art to which this invention pertains is the purification of a diolefin hydrocarbon stream containing trace quantities of acetylene compounds. The production of diolefins is well known and widely practiced to produce a wide variety of products and precursor products utilizing a variety of diolefin production processes including naphtha cracking processes and by-products from fluid catalytic cracking processes. Most of these diolefin production processes produce undesirable trace quantities of acetylene. One technique which is used to purify diolefin streams selectively hydrogenates the acetylene while minimizing the destruction or hydrogenation of the diolefin compounds.

The selective hydrogenation of the acetylene compounds is generally conducted in the presence of a selective hydrogenation catalyst and hydrogen and conducted at an elevated pressure and temperature. Such selective hydrogenation catalysts are well known in the art and include, for example, a catalyst containing copper metal associated with one or more activator metals impregnated on an alumina support. During the acetylene hydrogenation polymers are formed and deposited on the catalyst thereby reducing the activity of the catalyst. One known method of regenerating spent or partially spent catalyst is to perform a controlled carbon burn and subsequent metal reduction to remove catalyst contaminants which are formed as an undesirable by-product of the acetylene hydrogenation. The carbon burn regeneration techniques necessarily require that the reaction zone containing the spent catalyst be taken off-line and that ancillary regeneration equipment be provided.

INFORMATION DISCLOSURE

U.S. Pat. No. 3,634,536 (Frevel et al) discloses a process for selectively hydrogenating acetylenic impurities in an isopropene- or butadiene-containing stream whereby carbon monoxide is utilized during hydrogenation over a copper-based catalyst.

U.S. Pat. No. 4,440,956 (Couvillion) discloses a catalyst for the removal of acetylenes from liquid hydrocarbon streams with a minimum loss of diolefinic unsaturation present in the liquid composition.

Although a wide variety of process flow schemes, operating conditions and catalysts have been used in commercial activities, there is always a demand for new selective hydrotreating processes which provide lower costs, higher selectivity and longer on-stream operation.

The present invention continuously maintains the high activity of the selective hydrogenation catalyst during an extended run length without shutdown for catalyst regeneration. Higher average product quality when integrated over time on-stream improves the process economics and demonstrates the unexpected advantages.

BRIEF SUMMARY OF THE INVENTION

The present invention is a selective acetylene hydrogenation process which is able to produce a high quality diolefin having extremely low levels of acetylene over an extended period of time compared with the prior art. The process of the present invention provides a selective hydrogenation reaction zone wherein the catalyst activity is maintained at a high level while the process unit remains on stream by contacting the selective hydrogenation catalyst with a polymer solvent, diolefin feed and hydrogen.

In accordance with one embodiment, the present invention relates to a process for the purification of a diolefin hydrocarbon stream containing trace quantities of acetylene compounds which process comprises: (a) contacting the diolefin hydrocarbon stream containing trace quantities of acetylene compounds with a polymer solvent and introducing the resulting admixture together with elemental hydrogen into a selective hydrogenation zone to selectively hydrogenate at least a portion of the acetylene compounds; (b) passing the resulting effluent from the selective hydrogenation zone in step (a) to a fractionation zone to produce a diolefin hydrocarbon stream having a reduced concentration of acetylene compounds and a stream containing polymer solvent and polymer compounds; (c) recycling at least a portion of the stream containing polymer solvent and polymer compounds to provide at least a portion of the polymer solvent in step (a); (d) recovering at least another portion of the stream containing polymer solvent and polymer compounds; and (e) recovering the diolefin hydrocarbon stream having a reduced concentration of acetylene compounds produced in step (b).

In accordance with another embodiment, the present invention relates to a process for the purification of a butadiene hydrocarbon stream containing trace quantities of acetylene compounds which process comprises: (a) contacting the butadiene hydrocarbon stream containing trace quantities of acetylene compounds with a hexane solvent and introducing the resulting admixture together with elemental hydrogen into a selective hydrogenation zone containing a copper catalyst to selectively hydrogenate at least a portion of the acetylene compounds; (b) passing the resulting effluent from the selective hydrogenation zone in step (a) to a fractionation zone to produce a butadiene hydrocarbon stream having a reduced concentration of acetylene compounds and a stream containing hexane solvent and polymer compounds; (c) recycling at least a portion of the stream containing hexane and polymer compounds to provide at least a portion of the hexane solvent in step (a); (d) recovering at least another portion of the stream containing hexane solvent and polymer compounds; and (e) recovering the butadiene hydrocarbon stream having a reduced concentration of acetylene compounds produced in step (b).

BRIEF DESCRIPTION OF THE DRAWING

The drawing is a simplified process flow diagram of a preferred embodiment of the present invention. The drawing is intended to be schematically illustrative of the present invention and not be a limitation thereof.

DETAILED DESCRIPTION OF THE INVENTION

It has been discovered that a selective hydrogenation zone for the hydrogenation of trace quantities of acetylene contained in a stream of diolefins may achieve continued start-of-run activity, yields and product quality by contacting the selective catalyst with a polymer solvent, diolefin feed and hydrogen. These advantages enable superior performance and economic results.

The process of the present invention is particularly useful for the production of high quality diolefin streams in a process having an extended on-stream capability. The diolefin feed stream may be any convenient hydrocarbon stream containing diolefin compounds and having undesirable trace quantities of acetylene compounds. It is contemplated that the diolefin feedstream contains diolefins containing from 3 to about 5 carbon atoms. A preferred diolefin feedstream contains butadiene.

In accordance with the present invention, the selected diolefin feedstock is introduced along with a polymer solvent and hydrogen into a selective hydrogenation reaction zone operating at selective hydrogenation conditions and containing a selective hydrogenation catalyst to produce an improved diolefin stream having a reduced concentration of acetylene compounds.

The polymer solvent may be selected from any compound or mixtures of compounds and which polymer solvent is capable of acting as a solvent for polymers which are produced during the selective hydrogenation reaction. Suitable solvents may be selected from alkane compounds having from about 4 to about 8 or more carbon atoms. In the case where the fresh feedstock is a stream of butadiene, a particularly preferred polymer solvent is hexane. The polymer solvent may be present in an amount of about 5 to about 100 weight percent based on the weight of diolefin. It is preferred that the polymer solvent has a boiling point greater than the diolefin feedstream. The selective hydrogenation conditions will depend upon the selected diolefinic feed and may be selected from a pressure from about 200 psig to about 500 psig and a temperature from about 90° F. to about 180° F.

The resulting effluent from the selective hydrogenation reaction zone is passed to a fractionation zone to produce a diolefin hydrocarbon stream having a reduced concentration of acetylene compounds and a stream containing the polymer solvent and polymer compounds. A small drag stream of polymer solvent containing dissolved polymer compounds is removed from the process to prevent an accumulation of polymer compounds in the polymer solvent. Fresh make-up polymer solvent is added in order to maintain a suitable inventory of solvent. At least a portion of the polymer solvent recovered from the fractionation zone is recycled to the inlet of the selective hydrogenation zone.

The selective hydrogenation catalyst may be any suitable known catalyst and may contain one or more beds of the same or different selective hydrogenation catalyst. Suitable catalysts for the selective hydrogenation of acetylene contain copper metal, activated with one or more of the metals from the group of silver, platinum, palladium, manganese, cobalt, nickel, chromium and molybdenum on an alumina support. The hydrogenation catalysts contemplated for use in the process of the present include any support types, sizes and shapes, for example, spheres, cylinders, tri-lobes, quadralobes and rings. The process of the present invention is not limited by the type of hydrogenation catalyst and any suitable selective hydrogenation catalyst is contemplated for use therein.

DETAILED DESCRIPTION OF THE DRAWING

In the drawing, the process of the present invention is illustrated by means of a simplified schematic flow diagram in which such details as instrumentation, heat-exchange, and heat-recovery circuits, separation facilities and similar hardware have been deleted as being non-essential to an understanding of the techniques involved.

With reference now to the drawing, a feedstream comprising butadiene, trace quantities of acetylene and steam condensate is introduced into the process via line 1 and is passed into feed surge drum 2. A condensed steam stream is removed from feed surge drum 2 via line 3 and recovered. A stream containing butadiene and trace quantities of acetylene is removed from feed surge drum 2 via line 4 and is admixed with a recycle stream containing a polymer solvent transported via line 14 and the resulting admixture is transported via line 5 and is admixed with a hydrogen-rich gaseous stream provided via line 15 and the resulting admixture is transported via line 16 and introduced into selective hydrogenation zone 6. An effluent stream containing butadiene and having a reduced concentration of acetylene compounds is removed from selective hydrogenation zone 6 via line 7 and introduced into fractionation zone 8. A stream containing butadiene and having a reduced concentration of acetylene compounds is removed from fractionation zone 8 via line 9 and is recovered for further purification and subsequent use. A stream containing polymer solvent and polymer compounds is removed from fractionation zone 8 via line 10 and at least a portion is transported via line 11 and introduced into polymer solvent storage drum 13. Another portion of the stream removed from fractionation zone 8 via line 10 is removed via line 12 as a drag stream in order to prevent an undue accumulation of polymer compounds in the process. A stream containing polymer solvent and dissolved polymer compounds is removed from polymer solvent storage vessel 13 via line 14 and is admixed with a fresh make-up stream of polymer solvent which is introduced via line 17 and the resulting mixture is carried via line 14 and contacts the butadiene stream carried via line 4 as hereinabove described.

The process of the present invention is further demonstrated by the following illustrative embodiment. This illustrative embodiment is, however, not presented to unduly limit the process of this invention, but to further illustrate the advantages of the hereinabove-described embodiment. The following results were not obtained by the actual performance of the present invention but are considered prospective and reasonably illustrative of the expected performance of the invention based upon sound engineering calculations.

ILLUSTRATIVE EMBODIMENT

A raw butadiene stream in an amount of 100 mass units and having the characteristics presented in Table 1 is introduced into a fresh feed drum and entrained or condensed water is decanted therefrom. The raw butadiene stream is then admixed with 90 mass units of hexane solvent and the resulting mixture is introduced along with 1 mass units of hydrogen into a fixed bed of selective hydrogenation catalyst. The catalyst contains copper metal. The resulting effluent from the selective hydrogenation is introduced into a fractionation zone to produce a butadiene stream containing less than 3 wppm acetylene compounds (a 99.9% reduction). A bottoms stream containing polymer solvent and dissolved polymer was removed and introduced into a polymer solvent storage drum. A stream containing polymer solvent and polymers and in an amount of 0.35 mass units is removed from the process as a drag stream and recovered. Another stream containing polymer solvent and dissolved polymers is admixed with a fresh make-up stream of about 0.3 mass units and is introduced into the selective hydrogenation zone as described hereinabove. The selective hydrogenation zone is operated at conditions which are selected to selectively hydrogenate the acetylene compounds while minimizing any hydrogenation of the butadiene compounds including a temperature of about 95° F. and a pressure of about 400 psig.

TABLE 1

| RAW BUTADIENE STREAM ANALYSIS | |
|---|---|
| Butadiene | 50 weight % |
| Acetylene | 0.8 weight % |

The foregoing description, drawing and illustrative embodiment clearly illustrate the advantages encompassed by the process of the present invention and the benefits to be afforded with the use thereof.

What is claimed:

1. A process for the purification of a diolefin hydrocarbon stream containing trace quantities of acetylene compounds which process comprises:

(a) contacting said diolefin hydrocarbon stream containing trace quantities of acetylene compounds with a polymer solvent consisting essentially of an alkane compound having from about four to about eight carbon atoms and introducing the resulting admixture together with elemental hydrogen into a selective hydrogenation zone to selectively hydrogenate at least a portion of said acetylene compounds;

(b) passing the resulting effluent from said selective hydrogenation zone in step (a) to a fractionation zone to produce a diolefin hydrocarbon stream having a reduced concentration of acetylene compounds and a stream containing polymer solvent and polymer compounds;

(c) recycling at least a portion of said stream containing polymer solvent and polymer compounds to provide at least a portion of said polymer solvent in step (a);

(d) recovering at least another portion of said stream containing polymer solvent and polymer compounds; and (e) recovering said diolefin hydrocarbon stream having a reduced concentration of acetylene compounds produced in step (b).

2. The process of claim 1 wherein said diolefin stream comprises butadiene.

3. The process of claim 1 wherein said selective hydrogenation zone contains a catalyst comprising copper.

4. The process of claim 1 wherein said selective hydrogenation zone is operated at conditions including a pressure from about 200 to about 500 psig and a temperature from about 90° F. to about 180° F.

5. A process for the purification of a butadiene hydrocarbon stream containing trace quantities of acetylene compounds which process comprises:

(a) contacting said butadiene hydrocarbon stream containing trace quantities of acetylene compounds with a hexane solvent and introducing the resulting admixture together with elemental hydrogen into a selective hydrogenation zone containing a copper catalyst to selectively hydrogenate at least a portion of said acetylene compounds;

(b) passing the resulting effluent from said selective hydrogenation zone in step (a) to a fractionation zone to produce a butadiene hydrocarbon stream having a reduced concentration of acetylene compounds and a stream containing hexane solvent and polymer compounds;

(c) recycling at least a portion of said stream containing hexane and polymer compounds to provide at least a portion of said hexane solvent in step (a);

(d) recovering at least another portion of said stream containing hexane solvent and polymer compounds; and (e) recovering said butadiene hydrocarbon stream having a reduced concentration of acetylene compounds produced in step (b).

* * * * *